US00PP22149P2

(12) United States Plant Patent
van Kleinwee

(10) Patent No.: US PP22,149 P2
(45) Date of Patent: Sep. 13, 2011

(54) ***PETUNIA* PLANT NAMED 'PETPINVE'**

(50) Latin Name: *Petunia hybrida*
Varietal Denomination: Petpinve

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/803,463

(22) Filed: Jun. 28, 2010

(51) Int. Cl.
*A01H 5/00* (2006.01)

(52) U.S. Cl. ..... Plt./356.18

(58) Field of Classification Search ..... Plt./356.18, Plt./356.1

See application file for complete search history.

*Primary Examiner* — Annette Para

(74) *Attorney, Agent, or Firm* — S. Matthew Edwards

(57) ABSTRACT

A new *Petunia* plant named 'Petpinve' particularly distinguished by the large, light red-purple flowers with vivid purple veins, good floriferousness, medium green foliage, early flowering with a good center flowering habit, with good vigor, and exceptional branching with outwardly spreading plant habit.

1 Drawing Sheet

Latin name of the genus and species of the plant claimed: *Petunia hybrida.*

Varietal denomination: 'Petpinve'.

BACKGROUND OF THE NEW PLANT

The present invention comprises a new *Petunia*, botanically known as *Petunia hybrida*, and hereinafter referred to by the variety name 'Petpinve'.

'Petpinve' is a product of a planned breeding program. The new cultivar has large, light red-purple flowers with vivid purple veins, good floriferousness, medium green foliage, early flowering with a good center flowering habit, with good vigor, and exceptional branching with outwardly spreading plant habit.

'Petpinve' originated from a hybridization made in August 2004 in a controlled breeding environment in Enkhuizen, Netherlands. The female parent was the proprietary, unpatented plant designated 'D1278-1', with pink flowers.

The male parent of 'Petpinve' was the proprietary, unpatented plant designated 'C1380-1', with lavender flowers. The resultant seed was sown in February 2005 in Enkhuizen, Netherlands.

'Petpinve' was selected as one flowering plant within the progeny of the stated cross in the February 2005 in a controlled environment in Enkhuizen, Netherlands.

The first act of asexual reproduction of 'Petpinve' was accomplished when vegetative cuttings were propagated from the initial selection in May 2005 in a controlled environment in Enkhuizen, The Netherlands.

BRIEF SUMMARY OF INVENTION

Horticultural examination of plants grown from cuttings of the plant initiated in May 2005, and continuing thereafter, has demonstrated that the combination of characteristics as herein disclosed for 'Petpinve' are firmly fixed and are retained through successive generations of asexual reproduction.

'Petpinve' has not been observed under all possible environmental conditions. The phenotype may vary significantly with variations in environment such as temperature, light intensity and day length.

A Plant Breeder's Right for this cultivar was applied for in Canada on Feb. 9, 2010 (#10-6828). 'Petpinve' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Petpinve' with colors being as true as possible with an illustration of this type. The photographic drawing shows a flowering potted plant of the new variety and a close-up of the flowers growing in a 4 inch pot.

DETAILED BOTANICAL DESCRIPTION

The plant descriptions, measurements and aforementioned photographs were taken in Gilroy, Calif. from plants growing in a greenhouse trial in April 2010. These plants were approximately 13-14 weeks of age.

Color references are made to The Royal Horticultural Society Colour Chart (R.H.S.) 2001.

TABLE 1

DIFFERENCES BETWEEN THE NEW VARIETY 'PETPINVE' AND A SIMILAR VARIETY

| | 'Petpinve' | 'Pethorove' (U.S. Plant Pat. No. 20,989) |
|---|---|---|
| Flower color: | Light red-purple with vivid veins | More rosy red-purple |

TABLE 1-continued

DIFFERENCES BETWEEN THE NEW VARIETY 'PETPINVE' AND A SIMILAR VARIETY

| | 'Petpinve' | 'Pethorove' (U.S. Plant Pat. No. 20,989) |
|---|---|---|
| Peduncle length: | Somewhat shorter | Somewhat longer |
| Foliage color: | Medium green | Slightly more yellow-green |
| Petal apex: | More rounded | Less rounded |

Plant:

*Form, growth and habit.*—Initially upright, later on more trailing and outwardly spreading, good branching habit, pinching enhances development of lateral branches.

*Plant height.*—About 10 cm.

*Plant height (inflorescence included).*—About 20 cm.

*Plant width.*—35-42 cm.

Roots:

*Number of days to initiate roots and produce a rooted cutting.*—18-23 days at about 22 degrees C.

*Type.*—Fine, fibrous, free branching.

*Color.*—RHS N155B but whiter.

Foliage:

*Arrangement.*—Alternate, upper leaves sub-opposite.

*Immature, leaf color, upper surface.*—RHS 137A with slight RHS 146A blotches.

*Lower surface.*—RHS 137C.

*Mature, leaf color, upper surface.*—RHS 137A.

*Lower surface.*—Between RHS 137C and RHS 137D.

*Length.*—4.0-4.5 cm.

*Width.*—2.7-2.8 cm.

*Shape.*—Ovate.

*Base shape.*—Attenuate.

*Apex shape.*—Obtuse.

*Margin.*—Entire.

*Texture, upper surface.*—Glandular hairs; hirsute on veins and margins.

*Lower surface.*—Glandular hairs; hirsute on veins and margins.

*Color of veins, upper surface.*—RHS 144B becoming indistinct within the leaf blade.

*Color of veins, lower surface.*—RHS 144B.

*Petiole color.*—RHS 144B.

*Length.*—0.7-1.3 cm.

*Diameter.*—0.3 cm.

*Texture.*—Glandular hairs, hirsute.

Stem:

*Color of stem.*—RHS 146A.

*Length of stem.*—17-23 cm.

*Diameter.*—0.3 cm.

*Length of internodes.*—0.5-2.0 cm.

*Texture.*—Glandular hairs, pilose.

*Color of peduncle.*—RHS 146A to RHS 146B.

*Length of peduncle.*—3.5-3.8 cm.

*Peduncle diameter.*—0.2 cm.

*Texture.*—Glandular hairs, pilose.

Inflorescence:

*Type.*—Flowers appear solitary in upper leaf axis.

*Floret type.*—Funnel-shaped, 5 lobed petals, fused at the base, calyx, 5 deeply lobed sepals.

*Blooming habit.*—Continuous throughout the growing season. Good floriferousness.

*Quantity of inflorescences per plant.*—50-75 flowers plus numerous buds.

*Lastingness of individual blooms on the plant.*—5-7 days.

*Fragrance.*—Slightly sweet.

Bud (just before opening/showing color):

*Color.*—RHS 144C with about RHS 183D apex with darker veining, and a suffusion of RHS 183C basally.

*Length.*—2.0-3.5 cm.

*Width.*—0.4-0.7 cm.

*Shape.*—Oblong.

Immature inflorescence:

*Diameter.*—5.3 cm.

*Color, upper surface.*—Closest to RHS 69B overlaid with a hint of about RHS N74D, RHS N78A to RHS N78B at the margins, RHS N79A mid veins and RHS N78A veins.

*Lower surface.*—Closest to RHS 69D with a hint of RHS N74D, RHS N79B mid veins; weak RHS N79D veins.

Mature inflorescence:

*Floret horizontal diameter.*—6.0-6.7 cm.

*Vertical depth.*—5.5 cm.

*Petal color, upper surface.*—Closest to RHS 69C ground color overlaid with varing shades of RHS 84C to RHS 75C with hints of RHS N79B around the margins, RHS N79B mid-veins and RHS N79C veins.

*Lower surface.*—Closest to RHS 69D with a hint of RHS N74D, RHS N79B mid veins, weak RHS N79D veins.

*Petal apex shape.*—Rounded to obtuse.

*Petal base shape.*—Fused.

*Petal margin.*—Entire.

*Waviness of petals.*—Moderate.

*Petal lobation.*—Moderate.

*Petal texture, upper surface.*—Papillose.

*Under surface.*—Papillose.

*Corolla tube color inside.*—Closest to RHS 69D heavily overlaid with veining of RHS N79B to RHS N79D.

*Outside.*—Closest to RHS 69D with mid-veins of RHS N144C to RHS 144D and veins of RHS N79A.

*Corolla tube length.*—2.0-2.5 cm.

*Corolla texture, inside.*—Papillose.

*Outside.*—Long glandular hairs.

Calyx:

*Quantity of sepals.*—5.

*Color, upper surface.*—Closest to RHS 138A but darker.

*Lower surface.*—Closest to RHS 138A.

*Length.*—2.5 cm.

*Width.*—0.35-0.4 cm.

*Shape.*—Oblong.

*Apex shape.*—Acute to obtuse.

*Based.*—Fused.

*Margins.*—Entire.

*Texture, upper surface.*—Glandular hairs mainly at the margins.

*Lower surface.*—Glandular hairs mainly at the margins.

Reproductive organs:

*Pistil.*—1.

*Length,.*—2.2 cm.

*Style color.*—RHS 155C.

*Style length.*—1.8-1.9 cm.

*Stigma color.*—RHS N187A.

*Stigma shape.*—Oval.

*Ovary color.*—RHS 146B on upper half with RHS 151C on lower half.

*Stamens.*—5.

*Color of filaments.*—RHS 155C.
*Length filaments.*—1.2-1.4 cm.
*Anther color.*—RHS N187C to RHS 187D.
*Anther length.*—0.25 cm.
*Anther shape.*—Oval.
*Color of pollen.*—Lighter than RHS 202B.
*Pollen amount.*—Moderate.
*Fertility/seed set.*—Has not been observed on this hybrid.

Disease/pest resistance: Disease/pest resistance has not been observed on this hybrid.

What is claimed is:

1. A new and distinct variety of *Petunia* plant named 'Petpinve' substantially as illustrated and described herein.

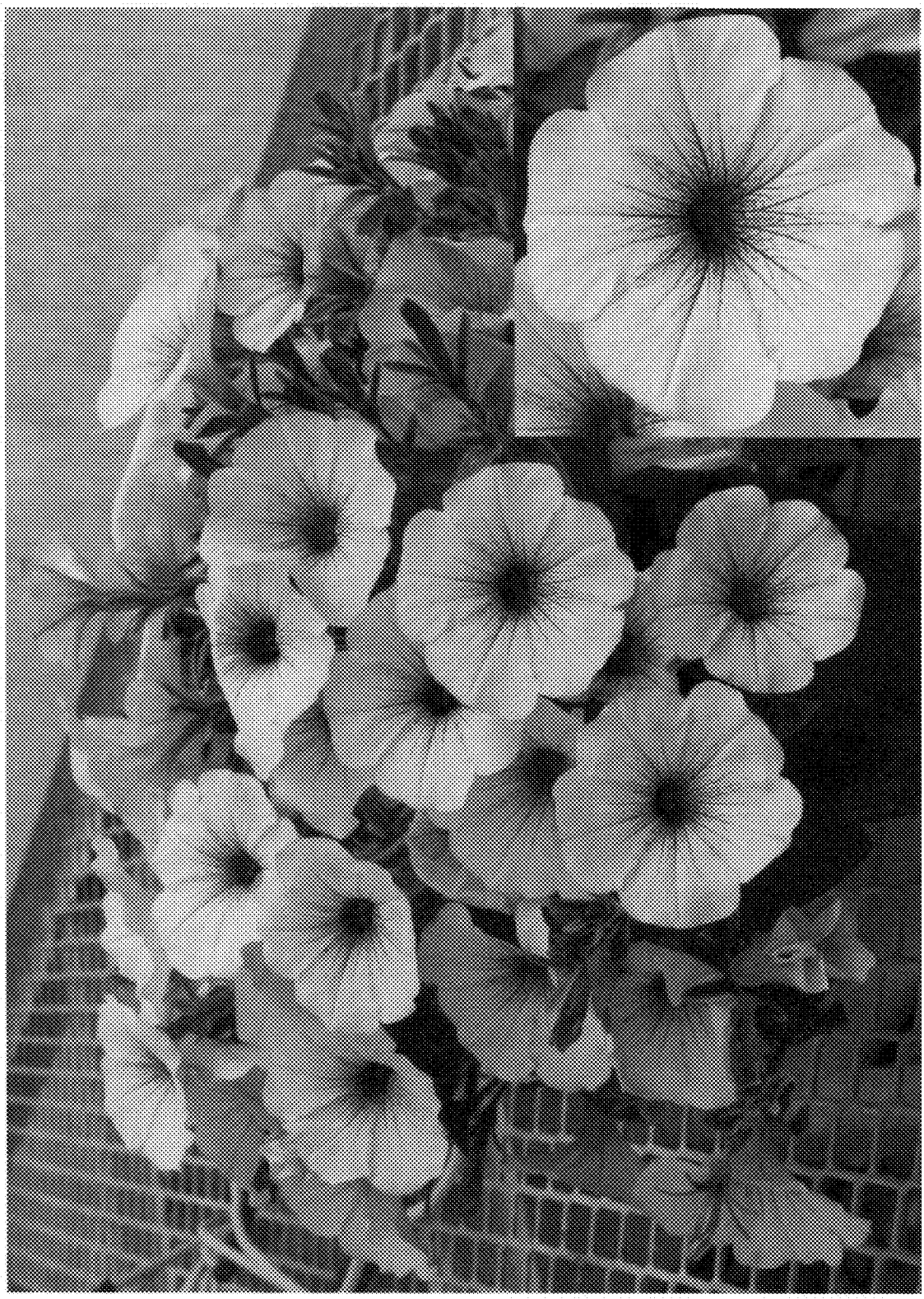

* * * * *